(12) United States Patent
Gerber et al.

(10) Patent No.: US 7,381,180 B2
(45) Date of Patent: Jun. 3, 2008

(54) IMPLANTABLE DEVICES AND METHODS FOR TREATING FECAL INCONTINENCE

(75) Inventors: Martin T. Gerber, Maple Grove, MN (US); Warren L. Starkebaum, Plymouth, MN (US); John M. Swoyer, Andover, MN (US)

(73) Assignee: Medtronic, Inc., Minneapolis, MN (US)

( * ) Notice: Subject to any disclaimer, the term of this patent is extended or adjusted under 35 U.S.C. 154(b) by 524 days.

(21) Appl. No.: 10/698,216

(22) Filed: Oct. 31, 2003

(65) Prior Publication Data
US 2005/0096497 A1    May 5, 2005

(51) Int. Cl.
*A61F 2/02* (2006.01)
(52) U.S. Cl. ............................................. 600/30
(58) Field of Classification Search ............... 600/9, 600/12, 15, 29–32; 623/13–14, 14.13; 604/96.01; 128/897–899
See application file for complete search history.

(56) References Cited

U.S. PATENT DOCUMENTS

| | | | |
|---|---|---|---|
| 4,979,947 A | | 12/1990 | Berman |
| 5,489,300 A | * | 2/1996 | Capecchi et al. ............ 128/898 |
| 5,542,799 A | * | 8/1996 | Culpen ....................... 411/271 |
| 5,704,893 A | | 1/1998 | Timm |
| 5,741,104 A | * | 4/1998 | Lat et al. .................... 411/453 |
| 5,792,478 A | | 8/1998 | Lawin et al. |
| 5,824,086 A | * | 10/1998 | Silvestrini .................. 623/5.11 |
| 6,090,063 A | | 7/2000 | Makower et al. |
| 6,098,629 A | * | 8/2000 | Johnson et al. ............. 128/897 |
| 6,190,684 B1 | | 2/2001 | Hench et al. |
| 6,231,613 B1 | | 5/2001 | Greff et al. |
| 6,251,063 B1 | * | 6/2001 | Silverman et al. ............ 600/29 |
| 6,277,392 B1 | | 8/2001 | Klein |
| 6,338,345 B1 | | 1/2002 | Johnson et al. |
| 6,354,991 B1 | | 3/2002 | Gross et al. |
| 6,358,197 B1 | * | 3/2002 | Silverman et al. ............ 600/29 |
| 6,401,718 B1 | | 6/2002 | Johnson et al. |
| 6,491,623 B2 | | 12/2002 | Snyder et al. |
| 6,533,717 B2 | | 3/2003 | Silverman et al. |
| 6,579,224 B1 | | 6/2003 | Burton et al. |
| 6,592,859 B1 | | 7/2003 | Bley |
| 6,595,910 B2 | | 7/2003 | Silverman et al. |
| 7,049,346 B1 | * | 5/2006 | Van Bladel et al. ......... 424/489 |
| 2001/0010021 A1 | * | 7/2001 | Boyd et al. .............. 623/17.13 |
| 2001/0046518 A1 | * | 11/2001 | Sawhney ..................... 424/486 |
| 2002/0072720 A1 | * | 6/2002 | Hague et al. ................ 604/264 |
| 2002/0091295 A1 | * | 7/2002 | Wilk ............................ 600/12 |
| 2002/0188308 A1 | * | 12/2002 | Tu et al. ..................... 606/167 |
| 2003/0018344 A1 | | 1/2003 | Kaji et al. |

FOREIGN PATENT DOCUMENTS

| | | |
|---|---|---|
| WO | 0232321 A | 4/2002 |
| WO | WO 02/32321 A1 * | 4/2002 |
| WO | 0211696 A | 8/2002 |

\* cited by examiner

*Primary Examiner*—Charles A. Marmor, II
*Assistant Examiner*—Christine D Hopkins
(74) *Attorney, Agent, or Firm*—Mary P. Bauman (57) ABSTRACT

In general, the invention is directed to treatment of fecal incontinence by the implantation of one or more bulking prostheses proximate to an anal sphincter. These bulking prostheses, which may include biocompatible hydrogel, are inserted into the tissue near the anus through a small opening in the mucosa. When inserted, the bulking prostheses are in a miniature state. Upon introduction into the body, the devices enter an enlarged state. In their enlarged state, the bulking prostheses supply extra bulk to the tissues proximate to the anal sphincters. With the extra bulk, the patient can exercise voluntary control over the external sphincter to close the anus and maintain fecal continence.

4 Claims, 6 Drawing Sheets

IMPLANTABLE DEVICES AND METHODS FOR TREATING FECAL INCONTINENCE

FIELD OF THE INVENTION

The invention relates to medical devices implantable in and near the gastrointestinal tract.

BACKGROUND

Fecal incontinence is the loss of voluntary control to retain feces in the rectum. Fecal incontinence may be the result of a number of causes, such as old age, disease or trauma. Some patients suffering from fecal incontinence may deal with the condition by performing exercises, utilizing biofeedback or managing the diet.

For some patients, however, such measures are ineffective. In a healthy human being, the internal and external anal sphincters contract to prevent the escape of waste, the external sphincter being under the voluntary control of the patient. In some patients, however, the patient may have some control over the external sphincter, but one or both sphincters lack sufficient bulk to close the anus and prevent the escape of fecal matter.

There have been many approaches addressing fecal incontinence. For example, U.S. Pat. No. 4,979,947 to Berman describes a continence device inserted into the anal canal. This device can be inserted to prevent leakage and removed to allow waste to pass. U.S. Pat. No. 6,491,623 to Snyder et al. discloses a surgically implantable cuff-like device that acts as an artificial sphincter. This device is implanted in a major surgical procedure, is not easily removable, and includes moving parts.

Other approaches involve implantation of materials to bulk up the region surrounding the anus. U.S. Pat. Nos. 6,533,717 and 6,595,910 to Silverman et al., for example, disclose a non-aqueous solution introduced into the rectal wall that forms a non-biodegradable solid. U.S. Pat. Nos. 5,792,478 to Lawin et al. and U.S. Pat. No. 6,190,684 to Hench et al. disclose addressing fecal incontinence by implantation of various solids in solution.

Table 1 below lists documents that disclose techniques for addressing fecal incontinence.

TABLE 1

| U.S. Pat. No. | Inventors | Title |
| --- | --- | --- |
| 6,595,910 | Silverman et al. | Method for Treating Fecal Incontinence |
| 6,579,224 | Burton et al. | Apparatus and Method for Inserting an Adjustable Implantable Genitourinary Device |
| 6,533,717 | Silverman et al. | Method for Treating Fecal Incontinence |
| 6,491,623 | Snyder et al. | Device for Preventing Fecal Incontinence |
| 6,354,991 | Gross et al. | Incontinence Treatment Device |
| 6,190,684 | Hench et al. | Injectable Bio-Active Glass in a Dextran Suspension |
| 6,090,063 | Makower et al. | Device, System and Method for Implantation of Filaments and Particles in the Body |
| 5,792,478 | Lawin et al. | Tissue Injectable Composition and Method of Use |
| 5,704,893 | Timm | Vessel Occlusive Apparatus and Method |
| 4,979,947 | Berman | Encapsulated Expandable Continence Device |

All documents listed in Table 1 above are hereby incorporated by reference herein in their respective entireties. As those of ordinary skill in the art will appreciate readily upon reading the Summary of the Invention, Detailed Description of the Preferred Embodiments and Claims set forth below, many of the devices and methods disclosed in the patents of Table 1 may be modified advantageously by using the techniques of the present invention.

SUMMARY OF THE INVENTION

The present invention is directed to devices and methods for addressing fecal incontinence. The invention has certain objects. That is, various embodiments of the present invention provide solutions to one or more problems existing in the prior art with respect to addressing fecal incontinence. The problems include, for example, effectiveness of the treatment, inconvenience to the patient, the invasiveness of surgery that may be required along with the associated recovery time, and risks associated with mechanical or electrical failure of implanted devices having moving parts or electrical components. In the case of some implanted materials or devices, there are risks associated with device migration, and the implanted materials or devices are not easily removable.

Various embodiments of the present invention have the object of solving at least one of the foregoing problems. In general, the invention provides for treatment of fecal incontinence by the implantation of one or more bulking prostheses proximate to an anal sphincter. These bulking prostheses are implanted in tissue proximate to an anal sphincter, such as a submucosa or a musculature underlying the submucosa, such as the internal or external anal sphincters. Typically a small hole is made in the in the skin or the mucosa near the anus, and one or more bulking prostheses are implanted through the hole. One exemplary procedure for implanting the bulking prostheses is via a syringe. Another exemplary procedure involves drawing the mucosa away from the underlying musculature, forming a pocket in the tissue, and implanting one or more bulking prostheses in the pocket. A further exemplary procedure involves inserting one or more bulking prostheses having sharpened tips into the tissue with an application device.

When implanted, the bulking prostheses are in a miniature state. Upon introduction into the body, the bulking prostheses enter an enlarged state. In their enlarged state, the bulking prostheses supply extra bulk to the tissues proximate to the anal sphincters. With the extra bulk, the patient can exercise voluntary control over the external sphincter to close the anus and maintain fecal continence. Bulking prostheses that include a biocompatible hydrogel material, for example, assume a miniature state for implantation, and upon implantation absorb the fluids of the body to assume an enlarged state. Bulking prostheses in the enlarged state may assume any number of shapes, such as capsule-shaped, cylindrical, spherical, egg-shaped, or a partial cylinder.

The invention includes embodiments directed to methods comprising implanting a bulking prosthesis in tissue proximate to an anal sphincter. The invention also includes embodiments directed to systems and apparatus for implanting bulking prostheses, configurations of the bulking prostheses themselves and techniques for making bulking prostheses.

Various embodiments of the invention may possess one or more features capable of fulfilling the objects outlined above. The various embodiments of the invention provide for less invasive surgical intervention than other surgical techniques. As a result, the implantations may be performed in less time and with less expense, and with reduced recovery time for the patient. In addition, bulking prostheses implanted according to the invention may be readily removed, if necessary. Also, once the implants are in place, no further maintenance is necessary, as the bulking prosthesis require no electrical power supply and have no coupled moving parts. Many embodiments of bulking prostheses are of a size that stay in place following implantation, and have less tendency to migrate.

The above summary of the present invention is not intended to describe each embodiment or every embodiment of the present invention or each and every feature of the invention. Advantages and attainments, together with a more complete understanding of the invention, will become apparent and appreciated by referring to the following detailed description and claims taken in conjunction with the accompanying drawings.

The details of one or more embodiments of the invention are set forth in the accompanying drawings and the description below. Other features, objects, and advantages of the invention will be apparent from the description and drawings, and from the claims.

DETAILED DESCRIPTION OF THE PREFERRED EMBODIMENTS

Figure 1:
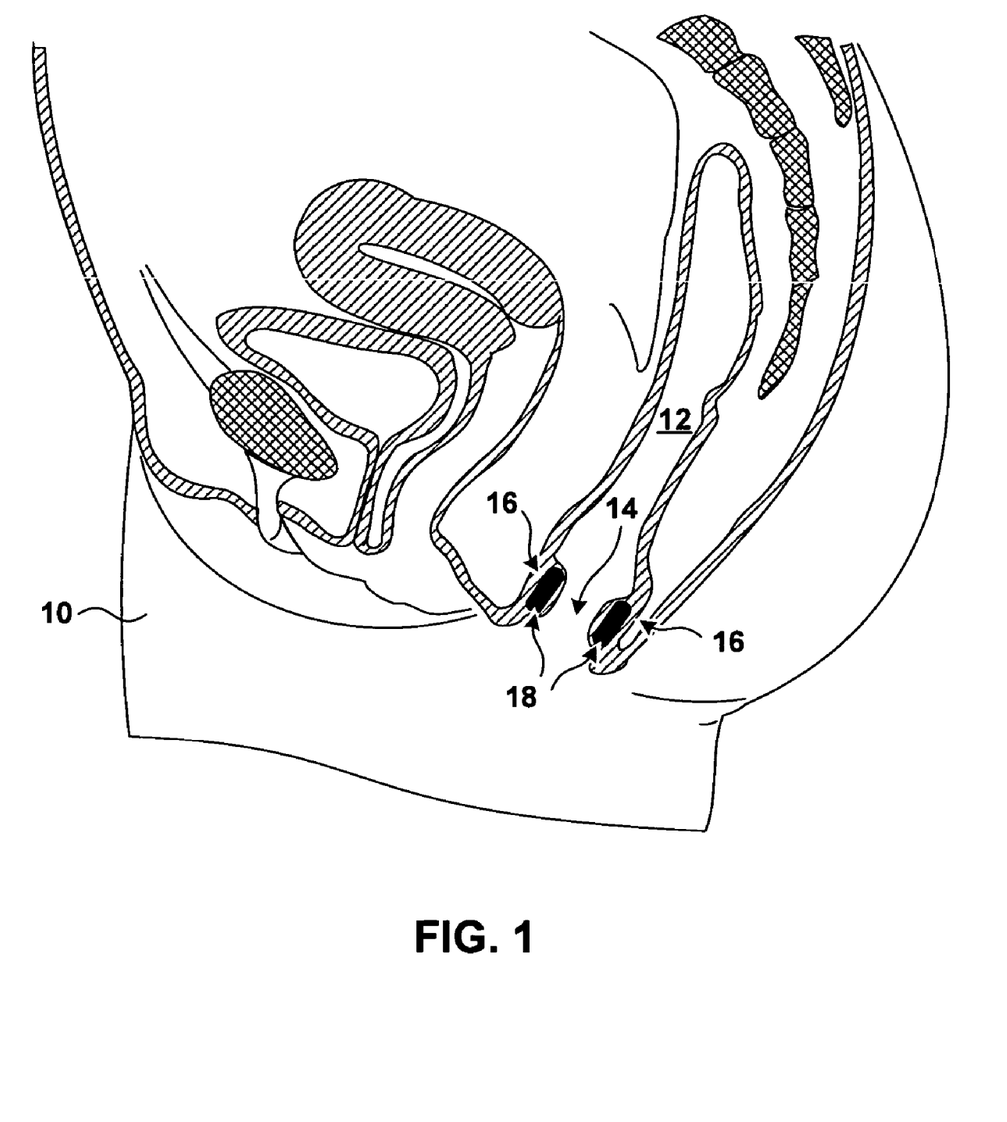
FIG. 1 is a sagittal cross section of a pelvic region of a patient, showing an exemplary placement of bulking prostheses.

FIG. 1 is a sagittal cross section of a pelvic region of a female patient 10. In FIG. 1, the rectum 12 of patient 10 extends inferiorly and terminates with the anal opening or anal canal 14. The anal walls 16 proximate to anal opening 14 include a mucosa (not shown in FIG. 1) proximate to anal opening 14, a submuscosa (not shown in FIG. 1) beneath the mucosa, and a musculature underlying the submucosa. The underlying musculature includes an internal anal sphincter (not shown in FIG. 1) and external anal sphincter (not shown in FIG. 1). The external anal sphincter, which is under the voluntary control of patient 10, is located more distally from anal opening 14 than is the internal anal sphincter.

FIG. 1 further shows bulking prostheses 18 implanted in the tissue of anal walls 16. Bulking prostheses 18 have been inserted in the tissue proximate to an anal sphincter. In the specific implantation shown in FIG. 1, bulking prostheses 18 have been implanted in the submucosa between the internal anal sphincter and the mucosa. In other implantations, bulking prostheses 18 may be implanted in or proximate to the musculature.

Patient 10 benefits from bulking prostheses 18 by being enabled to voluntarily control containment and release of feces. In the absence of bulking prostheses 18, a physical deficit causes patient 10 to experience fecal incontinence. The deficit may be caused by old age, disease, trauma or other cause. Although patient 10 retains some control over her external anal sphincter, she is unable to control containment and release of feces. With bulking prostheses 18 implanted in anal walls 16, however, patient 10 has more bulk proximate to anal opening 14, and is therefore able to exercise voluntary control over her external anal sphincter to close anal opening 14.

When implanted, bulking prostheses 18 were in a miniature state. Over time, bulking prostheses 18 swelled to an enlarged state. A bulking prosthesis may include a hydrogel material that, in the inert state free and of moisture, can be compressed into a miniature state. When placed in the body of patient 10, however, the hydrogel absorbs fluid from the body of patient 10 and swells to an enlarged state.

In particular, the bulking prosthesis in the miniature state comprises a substantially solid unhydraded hydrophilic polymer. Following implantation into the body of patient 10, however, the polymer absorbs water from the tissues of patient 10 to expand into an enlarged form and to form a colloidal gel in which the absorbed water is the dispersion medium. The bulking prosthesis may be formed from any of several biocompatible hydrogel materials, such as a multi-block polyacrylonitrile-based hydrogel material. Such a material, is commercially available as HYPAN™ from Lipo Chemicals, Inc. The bulking prosthesis may also include a radiopaque material, such as tantalum, to make the bulking prosthesis visible on an X-ray. Other radiopaque materials include barium sulfate, platinum or tungsten.

A bulking prostheses may be any number of shapes, such as capsule-shaped (i.e., shaped substantially like a medicine capsule or a grain of rice) or spherical. Other shapes for a bulking prostheses will be described below.

Figure 2:
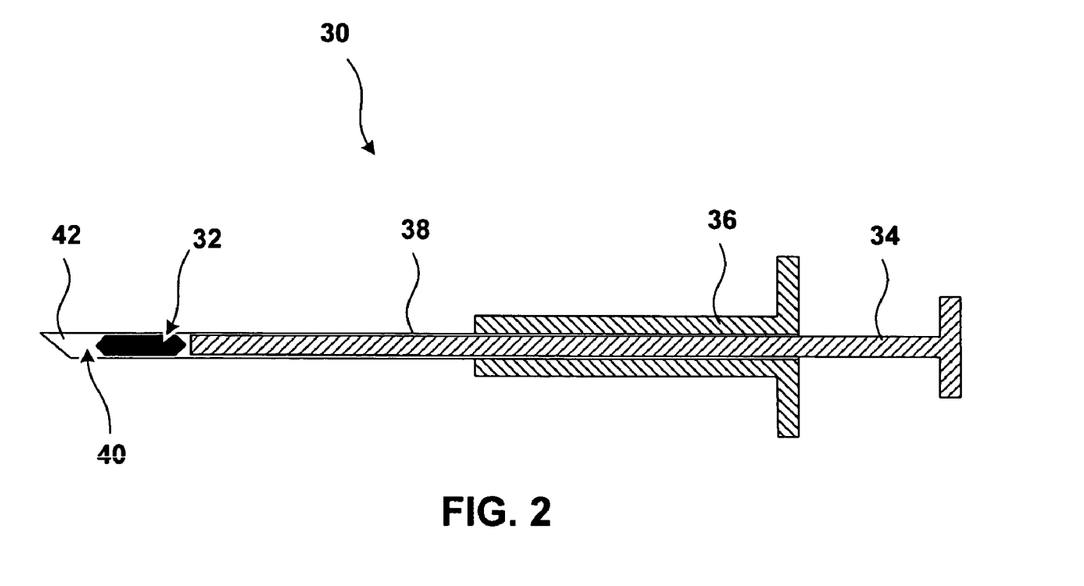
FIG. 2 is a cross section of an exemplary syringe that may be used to practice the invention.

FIG. 2 is a cross-sectional diagram of a device 30 that can implant a bulking prosthesis 32. Device 30 comprises a syringe, which includes a plunger member 34, a body member 36 and a hollow needle 38 having a lumen 40. Needle 38 is fixedly coupled to body member 36, while plunger member 34 is free to move in lumen 40. Lumen 40 of needle 38 has been enlarged to show bulking prosthesis 32, in a miniature state, disposed in lumen 40.

Distal end 42 of needle 38 includes a sharp point that can pierce tissue such as a mucosa proximate to an anal sphincter. Distal end 42 further includes an opening through which bulking prosthesis 32 may be expelled from lumen 40 by depressing plunger member 34 with respect to body member 36.

Figure 3:
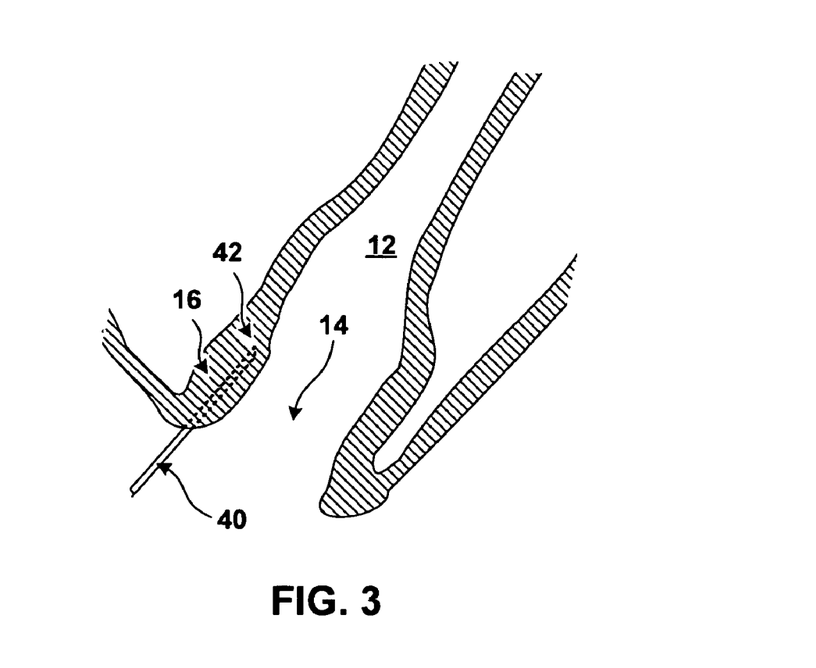
FIG. 3 is a sagittal cross section of an anal region, showing a technique for implantation of a bulking prosthesis with a needle such as the needle shown in FIG. 2.

FIG. 3 is a sagittal cross-section of an anal region, showing a technique for implantation of a bulking prosthesis with a needle such as needle 38 shown in FIG. 2. With the patient under general or local anesthesia, a physician inserts the needle 38 into the tissue proximate to the anal sphincters.

By depressing a plunger, the physician can expel a bulking prosthesis (not shown in FIG. 3) in a miniature state from distal end 42 of needle 38. Because the area around anal opening 14 is not a deep structure, the physician need not use an elaborate endoscope to implant the prosthesis in the desired area.

Figure 4:
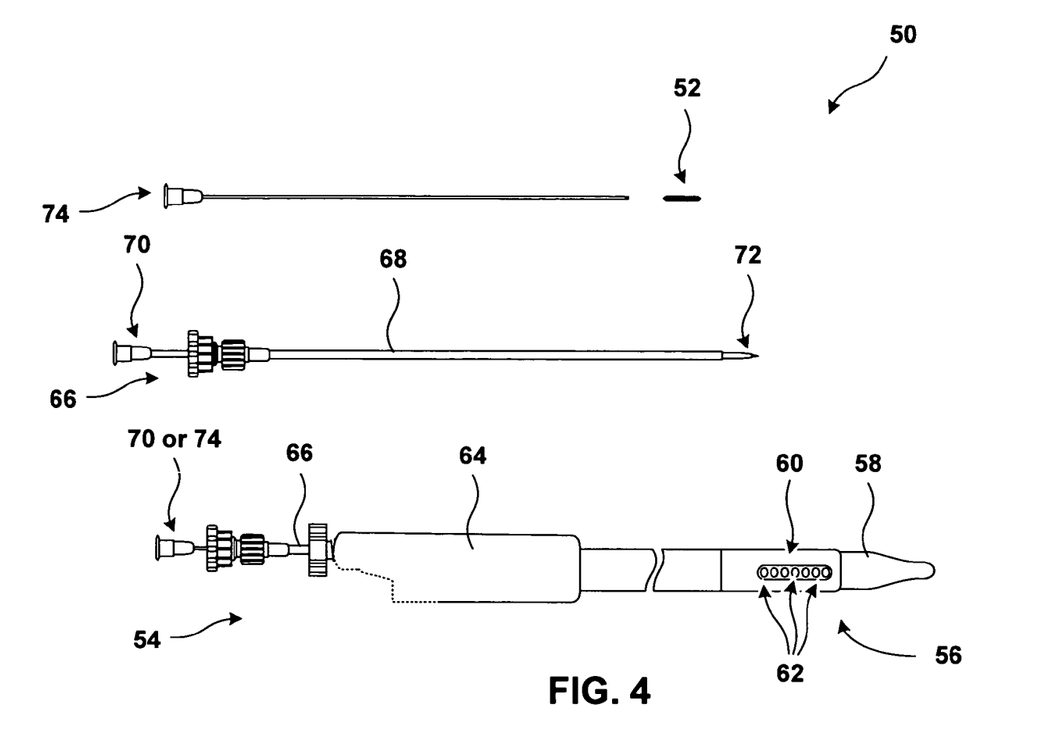
FIG. 4 is a plan view of components of a delivery apparatus that may be used to practice the invention.

FIG. 4 shows components of a delivery apparatus 50 that may be used to implant a bulking prosthesis 52 in a submucosa proximate to an anal sphincter. Delivery apparatus is embodied as an endoscopic device such as a Gatekeeper™ device commercially available from Medtronic, Inc. Delivery apparatus 50 includes an endoscopic member 54 that houses or receives the various components. Endoscopic member 54 includes a distal end 56 that is positioned by the physician proximate to the region of implantation. Distal end 56 includes a blunt tip 58 that provides an atraumatic surface and that protects the tissues of the patient upon insertion of distal end 56 into the body of the patient.

Distal end 56 also includes a lateral recess or cavity 60 to capture tissue such as a mucosa proximate to the site of implantation. Cavity 60 serves for positioning and implantation of bulking prosthesis 52, as described below. Cavity 60 includes a plurality of vacuum ports 62, which may be coupled to a source of vacuum pressure through the body of endoscopic member 54. Overtube 64 may include a coupling element (not shown) to couple delivery apparatus 50 to a source of vacuum pressure.

In FIG. 4, distal end 56 has been rotated to make cavity 60 and vacuum ports 62 visible. Cavity 60 defines a substantially rectangular orifice or recess with a major axis extending longitudinally relative to endoscopic member 54. Other shapes for cavity 60 are possible, however. In general, cavity 60 is sized and shaped to permit capture of a selected amount of mucosa to facilitate implantation of bulking prosthesis 52 below the mucosa. For example, cavity 60 may have different dimensions for implantation of bulking prostheses of different dimensions.

A sheath assembly 66 couples to endoscopic member 54. Sheath assembly 66 includes a sheathe 68 that receives one or more tools that are inserted into the body of the patient through endoscopic member 54. One tool that can be received in sheath 68 is a needle assembly 70. The distal end of needle assembly 70 includes a needle 72, which can penetrate and make a hole in a mucosa proximate to an anal sphincter. Another tool that can be received in sheath 68 is pushrod assembly 74. When bulking prosthesis 52 is inserted into sheath 68, pushrod assembly 74 drives bulking prosthesis 52 to the distal end of sheath 68. In a typical application, a physician makes a hole with needle 72 in a mucosa proximate to an anal sphincter, and pushes bulking prosthesis 52 through the hole with pushrod assembly 74.

Figure 5:
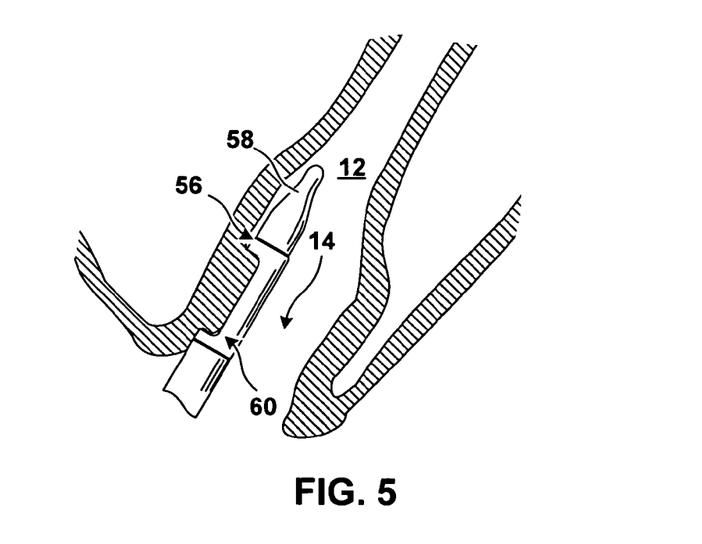
FIG. 5 is a sagittal cross section of an anal region, showing a technique for implantation of a bulking prosthesis with a delivery apparatus such as the delivery apparatus shown in FIG. 4.

FIG. 5 is a sagittal cross-section of an anal region, showing a technique for implantation of a bulking prosthesis with a device such as delivery apparatus 50 shown in FIG. 4. With the patient under general or local anesthesia, a physician inserts distal end 56 proximate to the anal sphincters and applies vacuum pressure from a vacuum source. The vacuum pressure draws the mucosal tissue into cavity 60. With mucosal tissue in cavity 60, a physician makes a hole with needle 72 in a mucosa and pushes bulking prosthesis 52 through the hole with pushrod assembly 74.

Figure 6:
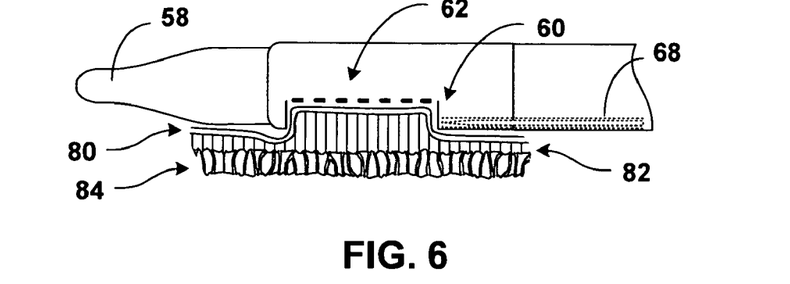
FIGS. 6-8 are side views of a delivery apparatus interacting with a mucosa proximate to an anal sphincter and implanting a bulking prosthesis, in a miniature state, in a submucosa proximate to an anal sphincter.
Figure 7:
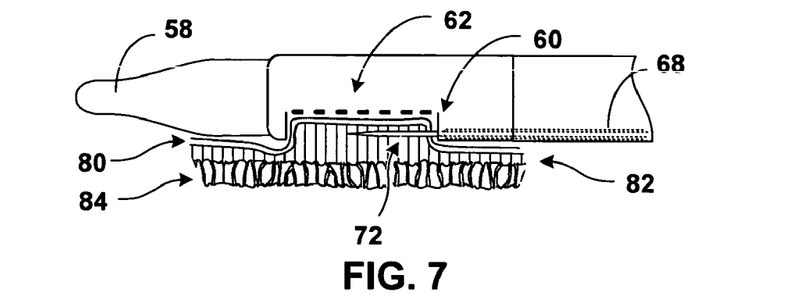
Figure 8:
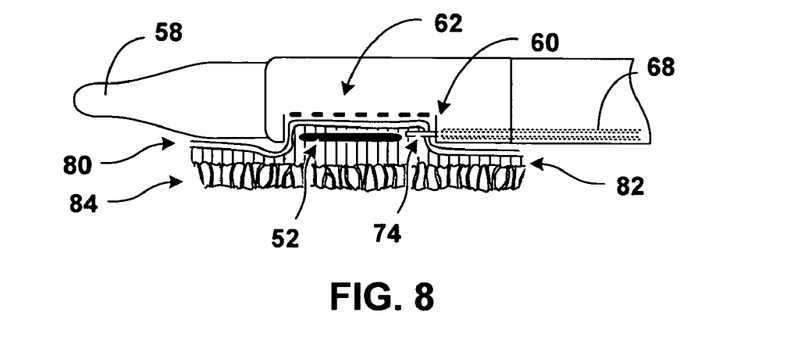

FIGS. 6-9 show a technique for implantation of a bulking prosthesis with a device as delivery apparatus 50. FIG. 6 depicts mucosa 80 drawn into cavity 60 by vacuum pressure applied via vacuum ports 62. With mucosal tissue in cavity 60, a physician makes a hole in mucosa 80 with needle 72, as shown in FIG. 7. The physician pushes needle assembly 70 through sheath 68, thereby making a hole in mucosa 80. Insertion of needle 72 through mucosa 80 causes needle 72 to form a pocket in the submucosa 82. This pocket, which receives bulking prosthesis 52, may be enlarged by injection of fluid, such as a saline solution, into the submucosa. The physician withdraws needle assembly 70 from sheath 68, and inserts bulking prosthesis 52 into sheath 68. The physician pushes bulking prosthesis 52 through the hole in mucosa 80 and into the pocket in submucosa 82 with pushrod assembly 74, as shown in FIG. 8. When implanted, bulking prosthesis 52 is in a miniature state. Bulking prosthesis 52 is implanted in submucosa 82 proximate to underlying musculature 84, which may be the external or internal anal sphincter. In some procedures, the physician forms a pocket in the musculature and implants bulking prosthesis 52 in the musculature 84.

Figure 9:
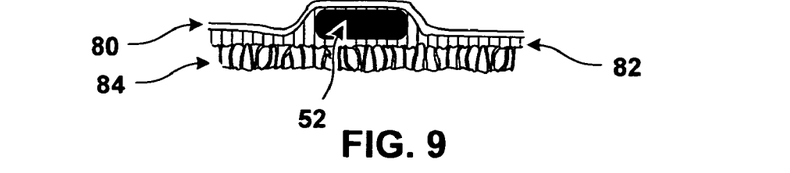
FIG. 9 is a view of a bulking prosthesis, in an enlarged state, implanted in a submucosa proximate to an anal sphincter.

As shown in FIG. 9, delivery apparatus 50 may be withdrawn following implantation. Over time, bulking prostheses 52 swells to an enlarged state, e.g., due to absorption of fluid from the body of the patient. With the extra bulk supplied by bulking prostheses 52 in its enlarged state, the patient can exercise voluntary control over the external sphincter to close the anus and maintain fecal continence.

A capsule-shaped bulking prosthesis, such as bulking prostheses 52 shown in FIG. 9, or a or substantially cylindrical bulking prosthesis, may have a diameter of two to twenty millimeters when in the enlarged state. In a typical application, the diameter of the bulking prosthesis may be four to ten millimeters. The length of the bulking prosthesis may be four to forty millimeters in the enlarged state, with a length of ten to twenty millimeters being typical. To provide sufficient bulking, it may be beneficial to implant a plurality of such bulking prostheses. A typical patient may receive two to eight bulking prostheses arrayed proximate to an anal sphincter, with four to six perhaps being more typical.

The implantation techniques shown in FIGS. 2-9 need not be limited to capsule-shaped or substantially cylindrical bulking prostheses, however. A bulking prostheses may assume other shapes as well. A hydrogel spherical bulking prosthesis, for example, may have a diameter of 0.2 millimeters to ten millimeters in the enlarged state, with a diameter of four to six millimeters being typical. A hydrogel bulking prosthesis may also be for example, egg-shaped, with dimensions comparable to that of a spherical or capsule-shaped bulking prosthesis. A typical patient may receive a plurality of bulking prostheses, with two to twenty bulking prostheses arrayed proximate to an anal sphincter.

Figure 10:
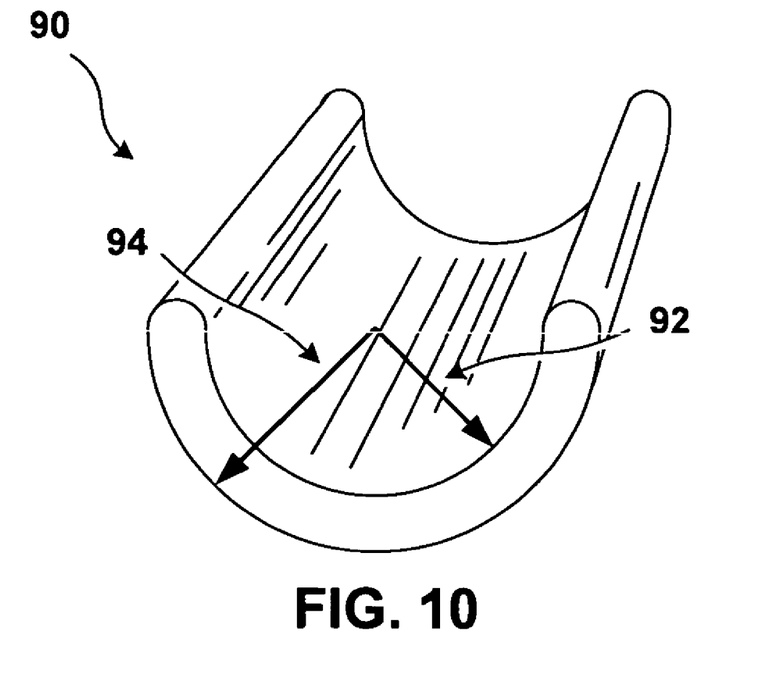
FIG. 10 is a perspective diagram of one embodiment of a bulking prosthesis in an enlarged state.
Figure 11:
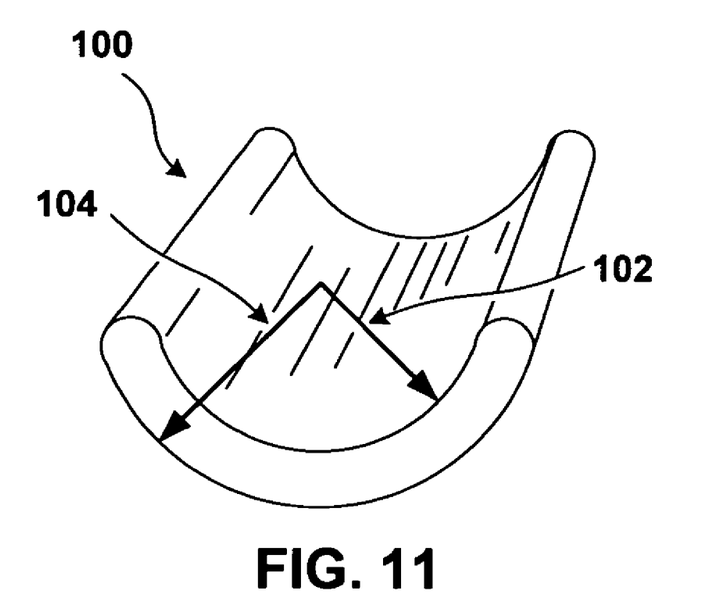
FIG. 11 is a perspective diagram of another embodiment of a bulking prosthesis in an enlarged state.

FIGS. 10 and 11 illustrate two other exemplary hydrogel bulking prostheses 90, 100. Bulking prostheses 90, 100 are shown in the enlarged state, and both are in the shape of a partial cylinder.

Bulking prosthesis 90 shown in FIG. 10 is substantially a half-cylinder, and has a C-shaped or "horseshoe" shaped cross-section. Bulking prosthesis 90 has an inner surface radius 92 that is sized to conform to close the anus of the patient when the patient exercises voluntary control over the external sphincter. Inner surface radius 92 is sized to the dimensions of the anus of a particular patient, with a typical inner surface radius 92 being in the range of six to twenty-five millimeters. The outer surface radius 94 of bulking prosthesis 90 is larger than inner surface radius 92 by about two to ten millimeters. The length of bulking prosthesis 90 may range from ten to forty millimeters. The cross-section of bulking prosthesis 90 need not be uniform, and bulking prosthesis 90 may resemble a curved wedge.

In a typical implantation, two half-cylinder bulking prostheses like bulking prosthesis 90 may be implanted in a patient on opposite sides of the anus. The two prostheses would not be coupled to one another, but their inner surfaces would be coaxial with the anus of the patient. When the patient exercises voluntary control over the external sphincter, the bulking prostheses supply the bulk to close the anus. When the patient needs to defecate, however, the patient can relax the external sphincter and allow the bulking prostheses to separate from one another, allowing the anus to open and waste to pass.

Bulking prosthesis 100 shown in FIG. 11 is a partial cylinder, and is less than a half-cylinder. Like bulking prosthesis 90, bulking prosthesis 100 has a C-shaped cross-section and an inner surface radius 102 that is sized to conform to close the anus of the patient when the patient exercises voluntary control over the external sphincter. In a typical implementation, inner surface radius 102 may be in the range of six to twenty-five millimeters, and the outer surface radius 104 of bulking prosthesis 100 may be larger than inner surface radius 102 by about two to ten millimeters. The length of bulking prosthesis 100 may range from ten to forty millimeters.

In a typical implantation, three or four bulking prostheses like bulking prosthesis 100 may be implanted in a patient around the anus. The inner surfaces of the prostheses would be coaxial with the anus of the patient. When the patient exercises voluntary control over the external sphincter, the bulking prostheses supply the bulk to close the anus. When the patient needs to defecate, however, the patient can relax the external sphincter and allow the bulking prostheses to separate from one another, allowing the anus to open and waste to pass.

Bulking prostheses 90 and 100 in FIGS. 10 and 11, when in a miniature state, need not be C-shaped. Rather, the prosthesis may be curled or folded to slide inside a needle such as needle 38 in FIG. 2, or a catheter or sheathe such as sheathe 68 in FIGS. 4 and 6-8.

Figure 12:
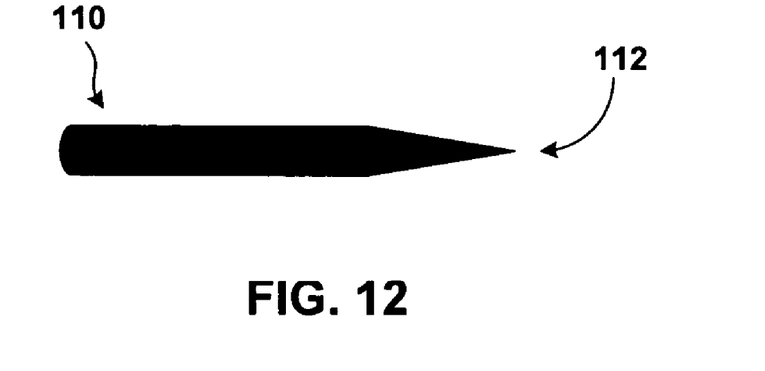
FIG. 12 is a side view of a bulking prosthesis having a sharpened tip.

FIG. 12 is a side view of a bulking prosthesis 110, in a miniature state. Bulking prosthesis 110 is made from a hydrogel material in the inert state, that is, bulking prosthesis 110 is formed from a hydrophilic polymer that forms a hydrogel in the presence of water. Bulking prosthesis 110 is substantially rod-like. Bulking prosthesis 110 in FIG. 12 is similar in construction and dimension to capsule-shaped bulking prostheses described above, but includes a sharpened tip 112. Tip 112 is sufficiently sharp to allow tip 112 to penetrate the tissues of a patient.

Although expanded hydrogel material is soft, inert hydrogel material can be rigid. In addition, the inert material can be machined to form a sharpened tip in any of a number of configurations. The sharpened tip may be conical, needle-like or wedge-shaped, for example. "Machining" includes any technique for forming a sharpened tip with an instrument, including cutting, grinding, honing and molding. Because the inert hydrogel material can be machined, other structures may be formed in addition to the sharpened tip, such as a slot on the end opposite the sharpened tip, or a helical thread around the bulking prosthesis. In one embodiment, the bulking prosthesis in the miniature state may resemble a screw.

Figure 13:
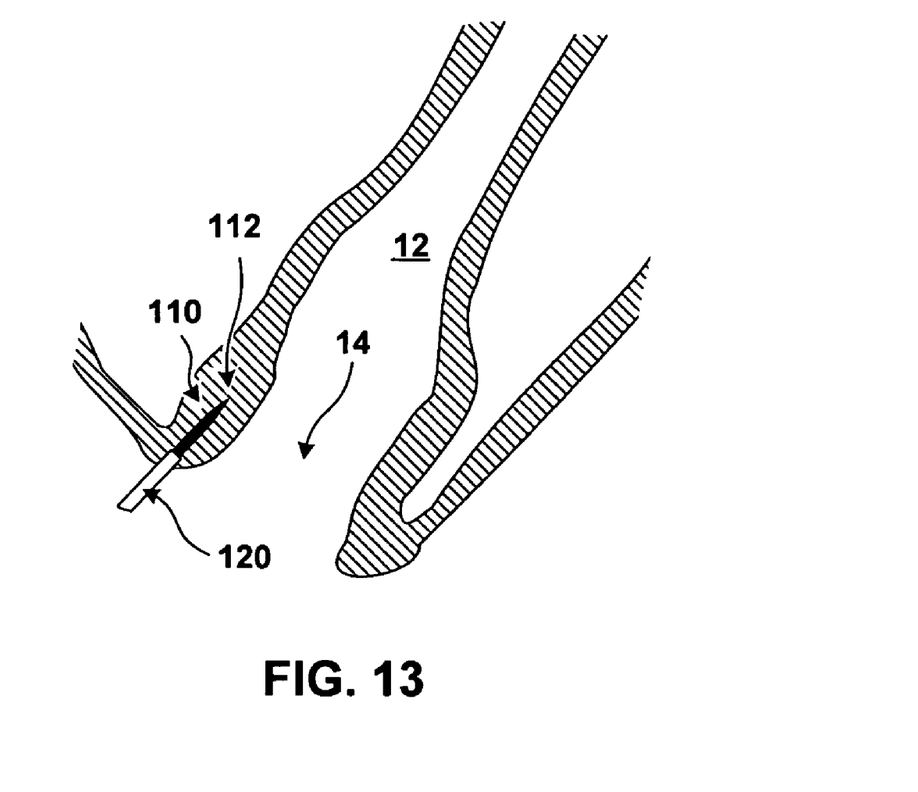
FIG. 13 is a sagittal cross section of an anal region, showing a technique for implantation of a bulking prosthesis with a sharpened tip, such as the bulking prosthesis shown in FIG. 12.

FIG. 13 is a sagittal cross-section of an anal region, showing a technique for implantation of a bulking prosthesis such as bulking prosthesis 110 shown in FIG. 12. With the patient under general or local anesthesia, a physician inserts the sharpened tip 112 of bulking prosthesis 110 into the tissue proximate to the anal sphincters. Bulking prosthesis 110 is engaged with an application device 120, which holds bulking prosthesis 110 and makes insertion easier. When bulking prosthesis 110 is in place, bulking prosthesis 110 disengages from application device 120, and application device 120 is withdrawn, leaving bulking prosthesis 110 in place.

Application device 120 may include a socket that temporarily holds, steadies or guides bulking prosthesis 110 during implantation. The particular configuration of an application device may depend upon the particular configuration of a bulking prosthesis. In the case of a bulking prosthesis that resembles a threaded screw, for example, the application device can be embodied as a screwdriver-like device that holds, steadies, guides and rotates the bulking prosthesis. An application device may also include apparatus, such as a plunger, to disengage the bulking prosthesis from the application device.

The invention may provide one or more advantages. Initial treatments for fecal incontinence tend to be conservative treatments, such as changing the diet of the patient or having the patient perform exercises. If the conservative treatments are unsuccessful, however, surgical intervention may be indicated. The invention provides for less invasive surgical intervention than other surgical techniques. As a result, the implantations may be performed in less time and with less expense, and with reduced recovery time for the patient. In addition, bulking prostheses implanted according to the invention may be readily removed, if necessary.

Once the implants are in place, no further maintenance is necessary. Unlike some fecal incontinence therapies, there is no need for an electrical supply, and there are no coupled moving parts. Many embodiments of bulking prostheses are of a size that stay in place following implantation. Larger bulking prostheses are less prone to migrate within the body of the patient.

Various embodiments of the invention have been described. Various modifications can be made to the described embodiments without departing from the scope of the invention. For example, the bulking prostheses may include a textured or porous surface to enhance stabilization or fixation. In one embodiment, a hydrogel bulking prosthesis may include a textured surface, and in another embodiment, the hydrogel or other hydrophilic polymer may be enclosed in a layer of porous material, such as Dacron mesh.

The dimensions of the bulking prostheses are for illustration, and the invention is not limited to the ranges of dimensions provided above. Nor is the invention strictly limited to the shapes described specifically above. For example, a substantially cylindrical or rod-shaped bulking prosthesis need not have a circular cross-section. The invention encompasses implantation techniques in addition to those described above. The invention further encompasses implantation of multiple prostheses at a single time, e.g., by implantation of two or more spherical bulking prostheses through the lumen of a syringe needle. These and other embodiments are within the scope of the following claims.

The invention claimed is:

1. A method for implanting a bulking prosthesis comprising:
   implanting a rod-like bulking prosthesis in a miniature state at the time of implantation and having a sharpened tip proximate to an anal sphincter, the bulking prosthesis engaged with an application device; and
   withdrawing the application device, wherein the bulking prosthesis assumes an enlarged state after implantation.

2. The method of claim 1, further comprising disengaging the bulking prosthesis from application device.

3. The method of claim 1, further comprising rotating the bulking prosthesis with the application device.

4. The method of claim 1, wherein the rod-like bulking prosthesis has a length of at least twenty millimeters when in the enlarged state.

* * * * *